(12) United States Patent
Barth et al.

(10) Patent No.: US 6,440,394 B2
(45) Date of Patent: Aug. 27, 2002

(54) REMINERALIZING-MINERALIZING ORAL PRODUCTS CONTAINING DISCRETE CATIONIC AND ANIONIC AGGLOMERATE COMPONENTS AND METHOD OF USE

(75) Inventors: Jordan Barth; Anthony E. Winston, both of East Brunswick; Norman Usen, Marlboro, all of NJ (US)

(73) Assignee: Church & Dwight, Co., Inc., Princeton, NJ (US)

( * ) Notice: Subject to any disclaimer, the term of this patent is extended or adjusted under 35 U.S.C. 154(b) by 0 days.

(21) Appl. No.: 09/893,019

(22) Filed: Jun. 26, 2001

Related U.S. Application Data

(63) Continuation of application No. 09/322,918, filed on Jun. 1, 1999, now abandoned.

(51) Int. Cl.$^7$ .......................... A61K 9/16; A61K 33/06; A61K 9/68
(52) U.S. Cl. .................. 424/48; 424/440; 426/3; 426/5
(58) Field of Search .................... 424/48, 440; 426/3–5

(56) References Cited

U.S. PATENT DOCUMENTS

| | | | |
|---|---|---|---|
| 3,954,649 A | * | 5/1976 | Lambert ...................... 252/126 |
| 4,001,448 A | * | 1/1977 | Finucane et al. ............ 426/285 |
| RE29,634 E | * | 5/1978 | Roberts et al. ................ 424/57 |
| 4,343,713 A | * | 8/1982 | Wise ............................ 252/92 |
| 4,397,837 A | * | 8/1983 | Raaf et al. ..................... 424/52 |
| 4,440,877 A | * | 4/1984 | Hauschild et al. ........... 523/105 |
| 4,444,570 A | * | 4/1984 | Barth et al. ................... 51/302 |
| 4,597,970 A | * | 7/1986 | Sharma et al. .................. 426/5 |
| 4,797,288 A | * | 1/1989 | Sharma et al. ............... 424/476 |
| 4,840,799 A | * | 6/1989 | Appelgren et al. .......... 426/493 |
| 4,866,023 A | * | 9/1989 | Ritter et al. .............. 502/17 X |
| 4,933,183 A | * | 6/1990 | Sharma et al. ............... 424/440 |
| 5,037,639 A | * | 8/1991 | Tung I .......................... 424/57 |
| 5,227,182 A | * | 7/1993 | Song et al. ..................... 426/5 |
| 5,268,167 A | * | 12/1993 | Tung II ........................ 424/52 |
| 5,534,244 A | * | 7/1996 | Tung III ....................... 424/52 |
| 5,571,502 A | * | 11/1996 | Winston et al. I ............. 426/52 |
| 5,582,855 A | * | 12/1996 | Cherukuri et al. .............. 426/5 |
| 5,614,175 A | * | 3/1997 | Winston et al. II ........... 426/52 |
| 5,833,954 A | * | 11/1998 | Chow et al. ................... 426/49 |
| 5,866,102 A | * | 2/1999 | Winston et al. III .......... 426/52 |
| 5,891,473 A | * | 4/1999 | Stanier ........................ 424/489 |

* cited by examiner

Primary Examiner—Shep K. Rose
(74) Attorney, Agent, or Firm—Stuart D. Frenkel

(57) ABSTRACT

A solid oral product, e.g., chewing gum, lozenge, an edible foodstuff, and the like, which is useful for remineralizing subsurface dental lesions and/or mineralizing exposed dentinal tubules, contains (A) a discrete cationic agglomerate component composed of at least one water-soluble or partially water-soluble calcium salt and a first inert solid carrier, and (B) a discrete anionic agglomerate component composed of at least one water-soluble orthophosphate salt and a second inert solid carrier. The agglomerate nature of the cationic and anionic components keeps these components separate from one another during storage of the product but allows the cationic and anionic salts to be simultaneously released from the product upon mixing of the product with water and/or saliva to form a mixed aqueous solution such that the solution contains both calcium cations released from the calcium salt and orthophosphate anions released by the orthophosphate salt.

20 Claims, No Drawings

REMINERALIZING-MINERALIZING ORAL PRODUCTS CONTAINING DISCRETE CATIONIC AND ANIONIC AGGLOMERATE COMPONENTS AND METHOD OF USE

This application is a continuation application of U.S. Ser. No. 09/322,918, filed Jun. 1, 1999 now abandoned.

BACKGROUND OF THE INVENTION

This invention is related to oral products capable of remineralizing subsurface dental lesions and/or mineralizing exposed dentinal tubules. More particularly, this invention is related to oral products capable of remineralizing subsurface dental lesions and/or mineralizing exposed dentinal tubules, wherein the oral products contain discrete cationic and anionic phases which do not react with one another prior to use of the product. This invention is further related to methods of using the oral products of this invention to remineralize subsurface dental lesions and/or mineralize exposed dentinal tubules.

The primary component of the enamel and dentin in teeth is calcium phosphate in the form of calcium hydroxyapatite. This material is highly insoluble at normal oral pHs but tends to dissolve in acidic media. Thus, when teeth are exposed to acids, e.g., acids generated during the bacteria-induced glycolysis of sugar in the oral cavity, lesions (i.e., demineralized areas) can form below the surface of intact enamel. Dental caries, the leading cause of tooth damage in humans, usually begins with these subsurface lesions, which are formed before a cavity is even detectable. If unchecked, the surface enamel above a subsurface lesion will eventually collapse, leading to cavitation and subsequent loss of tooth structure.

Subsurface remineralization can arrest and repair the carious lesions before any permanent structural damage to the tooth occurs. Unlike surface remineralization processes, which deposit calcium phosphate onto the tooth surface, subsurface remineralization processes precipitate calcium phosphate in the subsurface enamel where demineralization initially occurs.

Saliva is supersaturated with calcium and orthophosphate ions and, therefore, can help protect teeth against demineralization and remineralize teeth which have become demineralized. However, because saliva contains only modest levels of these ions, saliva-promoted remineralization tends to be slow.

The remineralization process can be speeded up by increasing the concentrations of dissolved calcium and orthophosphate ions in the oral cavity. However, this is not easy to do because, at the pH levels in the oral cavity, calcium and orthophosphate ions have a strong affinity for one another and tend to rapidly precipitate calcium phosphate. If such precipitation occurs too soon, subsurface remineralization, which requires that the calcium and orthophosphate ions remain soluble for a period of time sufficient to permit their diffusion into the demineralized subsurface of the dental enamel, will be reduced or prevented.

Thus, to achieve subsurface remineralization, precipitation of the calcium phosphate must be delayed until sufficient levels of the calcium and orthophosphate ions have reached the subsurface of the tooth.

A number of remineralizing products and methods have been developed which are designed at least in part to prevent premature reaction between calcium and orthophosphate ions used in such product or method. Reference is made, for example, to U.S. Pat. Nos. 4,083,955; 4,080,440; 4,606,912; 4,610,873; 4,397,837; 4,348,381; 4,177,258; 4,183,915; 4,460,565; 5,037,639; 5,268,167; 5,427,768; 5,437,857; and 5,460,803. Reference is also made to commonly assigned U.S. Pat. Nos. 5,571,502; 5,603,922; 5,605,675; 5,614,175; 5,645,853; 5,817,296; 5,833,957; 5,858,333; 5,866,102; and 5,895,641.

U.S. Pat. No. 4,083,955 (Grabenstetter et al.) discloses a method for remineralizing subsurface dental enamel, wherein a calcium salt solution and a phosphate salt solution are sequentially applied to dental enamel to effect subsurface remineralization thereof. The delivery system for the calcium and phosphate salt solutions can be in the form of two separate delivery vehicles, each containing one component, or in the form of a single delivery vehicle which contains both components but releases them sequentially. Examples of two-vehicle systems include mouthwash—mouthwash, toothpaste—toothpaste, candy drop—candy drop, nutritional substance—nutritional substance, and toothpowder—toothpowder. Examples of one-vehicle systems include a toothpaste wherein one ingredient is encapsulated for delayed release, a two-compartment bottle, a lozenge with a laminated structure so that first one ionic ingredient is released and then the other, a chewing gum made so that one ingredient is released before the other, and a nutritional substance in which one ingredient is released before the other.

U.S. Pat. No. 4,080,440 (DiGiulio et al.) discloses a method and a two-part product for remineralizing subsurface lesions in dental enamel, wherein the product contains a cationic part composed of a water-soluble calcium salt and an anionic part composed of a water-soluble phosphate salt. Remineralization is carried out by mixing a solution containing the cationic part with a solution containing the anionic part to form a metastable solution which is then promptly applied to the teeth. DiGiulio et al. teaches that the cationic and anionic parts are stored separately in the product to avoid premature precipitation of calcium phosphate. The product, examples of which include two-part mouthwashes and two-part toothpastes, may be in the form of a kit composed of separately packaged solutions of the respective cations and anions. As a two-part toothpaste, the product may be packaged in a codispensing toothpaste tube.

U.S. Pat. Nos. 4,606,912 and 4,610,873 (both to Rudy et al.) are each directed to an aqueous mouthwash solution which is maintainable as a one-bottle solution and capable of remineralizing caries lesions in teeth. The solution is made by forming an aqueous solution containing a source of calcium ions and a chelating agent for calcium ions, causing the chelation of at least 50% of the calcium ions, and subsequently adding a source of phosphate ions to the aqueous solution. The Rudy et al. patents teach that by bringing about the chelation of at least 50% of the calcium ions, the precipitation of calcium phosphate from the solution is avoided.

U.S. Pat. Nos. 4,177,258, 4,183,915 and 4,348,381 (all to Gaffar et al.) are each directed to stable, one-part aqueous compositions capable of remineralizing carious lesions in dental enamel and composed of a solution of water having dissolved therein a source of calcium ions and a source of phosphate ions, a fluoride compound and an antinucleating agent. The Gaffar et al. patents teach that the antinucleating agent prevents spontaneous precipitation of calcium phosphate on the enamel surfaces and thereby permits diffusion of the remineralizing components to the subsurface lesions. The Gaffar et al. patents further teach that the aqueous remineralizing composition is suitably prepared as a dental mouthrinse and also can be incorporated into other dentifrice compositions such as a dental cream or gel, mouth spray, troche, chewable tablet, lozenge and the like.

U.S. Pat. No. 4,460,565 (Weststrate et al.) discloses an anticariogenic remineralizing dentifrice containing two or more fluorine compounds, at least one water-soluble phosphate salt and at least one compound providing calcium ions. Examples of such dentifrices include toothpastes, prophylactic pastes, tooth polishes, mouth waters, application liquids, gels, and specific chewing gums. Weststrate et al. teaches that the specific calcium complexes used as the source of calcium ions therein are capable of retaining the calcium in an active form in dentifrices without deactivating the phosphate and fluoride ions.

U.S. Pat. Nos. 5,037,639; 5,268,167; 5,437,857; 5,427,768; and 5,460,803 (all to Tung) involve the use of amorphous calcium compounds such as amorphous calcium phosphate (ACP), amorphous calcium phosphate fluoride (ACPF) and amorphous calcium carbonate phosphate (ACCP) for use in remineralizing teeth. These amorphous compounds or solutions which form the amorphous compounds when applied either onto or into dental tissue prevent and/or repair dental weaknesses such as dental caries, exposed roots and dentin sensitivity. Remineralization is accomplished by bringing the amorphous compound into contact with the dental tissue. This can be done directly, i.e., putting an amorphous compound directly on the tooth, or indirectly through a carrier, i.e., incorporating the amorphous compound in a carrier such as a gel, a chewing gum, or a toothpaste and applying the carrier to the dental tissue. Once contact is established with the tooth, the amorphous calcium phosphate compounds will recrystallize to the less soluble apatite form in the lesion and reform the tooth. However, under conditions where amorphous calcium phosphate compounds are stable, the quantity of calcium and phosphate released is relatively low and, therefore, remineralization is slower than desirable. The Tung patents also teach the use of two-part solutions wherein a first part contains phosphate salt(s) and a second part contains calcium salt(s), wherein either the first part or the second part further contains carbonate salt(s). In addition, the Tung patents teach solutions formed by dissolving in water a solid powder containing calcium salt(s), phosphate salt(s), and carbonate salt(s). These solutions are then applied to dental tissue. The Tung patents further teach the use of non-carbonated solid powders containing mixtures of calcium salts and phosphate salts which can be applied directly to the tooth or dispersed in gel, chewing gum, or other non-aqueous mediums such as toothpaste which is placed in contact with the tooth.

U.S. Pat. Nos. 5,603,922, 5,817,296, 5,833,957 and 5,858,333 (all to Winston et al.) each disclose one-part and/or two-part products and methods of using same to remineralize subsurface lesions. The one-part and two-part products contain at least one water-soluble calcium salt, at least one water-soluble divalent metal salt wherein the divalent metal is other than calcium and at least one water-soluble phosphate salt. In the two-part products, the calcium and divalent metal salts are disposed in a first discrete component, and the phosphate salt(s) is disposed in a second discrete component.

U.S. Pat. Nos. 5,605,675 and 5,895,641 to Usen et al. disclose a two-part product and method of using same for remineralizing dental enamel, wherein the product contains a first discrete component containing at least one water-soluble calcium salt and a second discrete component containing at least one water-soluble phosphate salt and at least one water-soluble fluoride salt.

U.S. Pat. No. 5,645,853 to Winston et al. is directed to a chewing gum product and method of using same for remineralizing subsurface lesions in teeth, wherein the product contains a water-soluble cationic portion composed of at least one water-soluble calcium salt and at least one water-soluble, non-toxic divalent metal salt wherein the divalent metal is other than calcium; a water-soluble anionic portion containing at least one water-soluble phosphate salt; and a gum base.

U.S. Pat. Nos. 5,571,502, 5,614,175 and 5,866,102 (all to Winston et al.) are each directed to one-part, non-aqueous products and methods of using same for remineralizing subsurface lesions, wherein the products contain at least one water-soluble calcium salt; at least one water-soluble phosphate salt; either a stabilizer or a hydrophilic, non-aqueous, water-soluble vehicle; and, optionally, at least one water-soluble fluoride salt. When the components are mixed with water or saliva to form an aqueous mixed solution, the solution has a pH of from about 4.5 to about 10.0.

Although the aforementioned patents disclose various ways of keeping the calcium and phosphate ions separate from one another during storage of the product, it would be desirable to provide an easier and less expensive way of keeping the calcium and phosphate ions separate before use.

Particularly useful oral products for delivering remineralizing/mineralizing components to the teeth are chewing gum products. This is because the inherent nature of chewing gums allows prolonged contact with the teeth and further because the gum base can provide sustained release of the remineralizing/mineralizing components, thereby minimizing the amount of such components that must be used.

Several of the aforementioned patents disclose the use of remineralizing/mineralizing chewing gum products and other solid oral products. Non-limiting examples of other patents which teach the use of chewing gums or other solid oral products to deliver active components to teeth include U.S. Pat. Nos. 4,233,288; 4,828,845; 4,405,600; 5,204,115; 4,153,732; 3,892,843; 4,906,455; 4,902,498; 5,496,558; and 5,380,530.

Thus, it would be desirable to provide a chewing gum product, as well as other solid oral products, which contain remineralizing-mineralizing cationic and anionic salts, wherein the chewing gum product uses relatively inexpensive and easy means for keeping the salts separate from another during storage of the product.

Accordingly, a primary object of this invention is to provide an oral product capable of remineralizing subsurface dental lesions and capable of mineralizing exposed dentinal tubules and composed of water-soluble calcium and phosphate salts, wherein the product uses relatively inexpensive and easy means to keep the salts separate from one another in the product.

A further object of this invention is to provide an oral product having the aforementioned characteristics, wherein the product is a solid oral product such as, e.g., a chewing gum product, a lozenge, a candy product, an edible foodstuff, a toothpowder, and the like.

A still further object of this invention is to provide a method of remineralizing subsurface dental lesions and/or mineralizing exposed dentinal tubules, using an oral product having the aforementioned characteristics.

These and other objects which are achieved according to the present invention can be discerned from the following description.

SUMMARY OF THE INVENTION

In the present invention, remineralizing-mineralizing cationic and anionic salts are kept from reacting with one another prior to use of the oral product by disposing these salts as separate cationic and anionic agglomerates in the product. The agglomerated nature of the cationic and anionic salts allows these salts to be effectively separated from one another during storage of the product but also allows these salts to be simultaneously released from the product upon contact with water, such as, e.g., by chewing, sucking or eating.

Thus, in one aspect thereof, the present invention provides a solid oral product capable of remineralizing subsurface dental lesions and capable of mineralizing exposed dentinal tubules, containing:

(A) a discrete cationic agglomerate component composed of a remineralizing-mineralizing amount of at least one water-soluble or partially water-soluble calcium salt and a first inert solid carrier, and (B) a discrete anionic agglomerate component composed of a remineralizing-mineralizing amount of at least one water-soluble orthophosphate salt and a second inert solid carrier;

wherein components (A) and (B) have a pH in water such that a mixed aqueous solution formed by mixing components (A) and (B) with water and/or saliva has a pH of from about 4.5 to about 10.0;

further wherein the cationic and anionic agglomerate components are simultaneously releasable from the product upon mixing of the product with water and/or saliva to form the mixed aqueous solution such that the mixed aqueous solution contains calcium cations released from the calcium salt and orthophosphate anions released by the orthophosphate salt.

The solid oral product of this invention may be in the form of a chewing gum, a lozenge, a candy, an edible foodstuff, a tablet, a toothpowder, and the like.

Another aspect of the present invention is directed to a method of using the solid oral product of this invention to remineralize at least one subsurface dental lesion and/or mineralize at least one exposed dentinal tubule in at least one tooth. Such method involves the steps of:

(1) providing the oral product of this invention;

(2) contacting the product with water and/or saliva so as to form a mixed aqueous solution having a pH of from about 4.5 to about 10.0 and containing calcium cations released by the calcium salt and orthophosphate ions released by the orthophosphate salt; and (3) contacting the at least one tooth with the mixed aqueous solution for a period of time sufficient to allow a remineralizing/mineralizing amount of the calcium anions and a remineralizing/mineralizing amount of the orthophosphate anions to diffuse through the tooth to a subsurface thereof, wherein the diffused calcium cations and the diffused orthophosphate anions react together to form calcium hydroxyapatite onto the subsurface lesion and/or onto the exposed dentinal tubule, thereby remineralizing the lesion and/or mineralizing the exposed dentinal tubule.

If the product is a chewing gum, step (2) of the method of this invention involves chewing the product to release the calcium and orthophosphate salts. If the product is a lozenge, step (2) involves sucking the product. If the product is an edible foodstuff, step (2) involves eating the product.

DETAILED DESCRIPTION OF THE INVENTION

As stated above, the present invention is directed to solid oral products and methods of using same to remineralize subsurface dental lesions and/or to mineralize exposed dentinal tubules.

As used herein, the term "solid oral product" refers to a product which can be sucked, chewed or eaten. Non-limiting examples of such products include chewing gums, lozenges, candies, food products, dragees, bon bons, toothpowders, and the like.

The oral product of this invention contains a discrete cationic agglomerate component and a discrete anionic agglomerate component. The discrete cationic agglomerate component contains a remineralizing-mineralizing amount of at least one water-soluble or partially water-soluble calcium salt and may contain one or more non-toxic, water-soluble salts of a divalent metal other than calcium. The discrete anionic agglomerate component contains a remineralizing-mineralizing amount of at least one water-soluble orthophosphate salt and, optionally, at least one water-soluble fluoride salt.

With respect to the amounts of the calcium and orthophosphate salts, the term "remineralizing-mineralizing amount" means that amount which is sufficient to effect substantial remineralization of subsurface lesions in teeth and/or to effect substantial mineralization of exposed dentinal tubules.

As used herein with respect to the partially water-soluble calcium salt(s), the term "partially water-soluble" refers to a calcium salt having a solubility which is greater than that of dicalcium phosphate dihydrate in an aqueous solution having a pH of about 7.0 and a temperature of about 25° C. but which is less than that solubility which would release more than about 1400 ppm of calcium cations in such aqueous solution. In an aqueous solution having a pH of about 7.0 at a temperature of about 25° C., dicalcium phosphate dihydrate can release up to about 40 ppm of calcium cations by weight of the aqueous solution. Thus, partially water-soluble calcium salts useful in the oral product of this invention include calcium salts having a solubility in water such that the salt is capable of releasing more than about 40 ppm but no more than about 1400 ppm, preferably from about 100 ppm to no more than about 1400 ppm, of calcium cations by weight of an aqueous solution having a pH of about 7.0 at a temperature of about 25° C. As used herein with respect to the water-soluble calcium salt(s), water-soluble orthophosphate salt(s), water-soluble non-calcium divalent metal salt(s) and water-soluble fluoride salt(s), the term "water-soluble" refers to a solubility in water such that the salt is capable of releasing at least about 1400 ppm by weight of ions into an aqueous solution having a temperature of about 25° C. and a pH of about 7.0.

As will be discussed in greater detail hereinbelow, the oral products of this invention are made by forming separate agglomerates of the calcium and orthophosphate salts in combination with other dry, inert materials and carriers such as, e.g., sorbitol, mannitol, silicas, insoluble calcium phosphates, and the like. The agglomerate composed of the calcium salt(s) may further contain the non-calcium divalent metal salt(s), while the agglomerate containing the orthophosphate salt(s) may also contain the water-soluble fluoride salt(s). The agglomerate containing the calcium salt(s) is referred to herein as the "cationic agglomerate" or the "cationic agglomerate component", while the agglomerate containing the orthophosphate salt(s) is referred to herein as the "anionic agglomerate" or the "anionic agglomerate component".

The cationic and anionic agglomerates are then incorporated into a basic solid oral product, e.g., chewing gum, lozenge, and the like, to form the remineralizing/mineralizing final solid oral product of this invention. As used herein, the term "basic solid oral product" refers to a solid oral product to which the agglomerates of this invention have not been added.

The cationic and anionic agglomerates used in the present invention may be made by several different methods including, e.g., direct compression (i.e., dry agglomeration) methods, wet granulation methods, and absorption methods (involving absorption onto inert substances).

In direct compression methods, the calcium salt is intimately mixed with a first inert carrier, and the orthophosphate salt is intimately mixed with a second inert carrier. Each mixture is then compressed into dry flakes, tablets or agglomerates using, e.g., a tablet press or a Chilsonator. The resulting solids are then ground to the desired agglomerate size and added to a basic solid oral product (which has been formed according to known methods) to form the final product of this invention.

The most preferred inert carriers for use in direct compression processes are sorbitol, mannitol and xylitol.

In wet granulation processes, the calcium salt and a first inert carrier are placed in a mixer/agglomerator, and the orthophosphate salt and a second inert carrier are placed in a separate mixer/agglomerator. The two sets of materials then undergo mixing and agglomeration in the presence of water or other liquid. The powdered materials being agglomerated or the liquid being added preferably contains a binder to hold the agglomerated material together after drying. Suitable binders include, for example, PVP, polyvinyl acetate (PVA) or carboxymethylcellulose (CMC). The calcium-containing product and the phosphate-containing product are then dried and ground to the desired particle size. The particles are then added to a basic solid oral product to form the final product.

For wet agglomeration processes, the preferred inert carriers are insoluble materials such as, e.g., silicas or insoluble calcium phosphates. Non-limiting examples of suitable insoluble calcium phosphates include dicalcium phosphate dihydrate, anhydrous dicalcium phosphate, tricalcium phosphate and calcium hydroxyapatite.

Another method for making the agglomerates used in the present invention involves absorbing the calcium salt (and non-calcium divalent metal salt, if present) and the orthophosphate salt (and the fluoride salt, if present) onto separate inert substances. For example, the calcium and orthophosphate salts can be dissolved separately in water and the resulting solutions each added, with mixing, to an absorbent material of an appropriate particle size. If desired, PVP, CMC or other polymer can be included in the respective solutions to form a soluble film around the particles or to promote agglomeration of the absorbing particles. The materials are then dried and added to a basic solid oral product to form the final product.

The agglomerated particles used in the present invention preferably have a particle size of from about 100 to about 2000 microns. For smooth oral products, the particle sizes preferably range from about 400 to about 840 microns. For crunchy oral products, the particle sizes preferably range from about 840 to about 2000 microns.

As stated above, the cationic agglomerate component used in this invention contains at least one water-soluble or partially water-soluble calcium salt, and the anionic agglomerate component contains at least one water-soluble orthophosphate salt.

Non-limiting examples of partially water-soluble calcium salts suitable for use in this invention include calcium sulfate, anhydrous calcium sulfate, calcium sulfate hemihydrate, calcium sulfate dihydrate, calcium malate, calcium tartrate, calcium malonate, calcium succinate, and mixtures of the foregoing. Calcium sulfate is preferred.

Partially water-soluble calcium salts can be prepared in situ, for example, by preparing mixtures of an acid such as, e.g., tartaric acid, and a water-soluble calcium salt such as, e.g., calcium nitrate, and adjusting the pH as needed.

Non-limiting examples of water-soluble calcium salts useful in the product of this invention include, for example, calcium chloride, calcium lactate, calcium nitrate, calcium acetate, and calcium gluconate. Calcium lactate is preferred.

Mixtures of water-soluble and partially water-soluble calcium salts may be used in the oral product of this invention.

Suitable water-soluble inorganic orthophosphate salts for use in the present invention include, for example, alkali salts and ammonium salts of orthophosphoric acid, such as, e.g., potassium, sodium or ammonium orthophosphate; monopotassium orthophosphate; dipotassium orthophosphate; tripotassium orthophosphate; monosodium orthophosphate; disodium orthophosphate and trisodium orthophosphate.

As stated previously herein, the cationic agglomerate component may further contain one or more non-toxic, divalent metal salts other than calcium salt. Such salts release divalent metal cations which help to stabilize the mixed aqueous solution against rapid precipitation of the calcium cations and the phosphate and fluoride anions (if present). The remineralizing cations and anions can then diffuse through the tooth surface to the demineralized subsurface lesion(s) and/or the exposed dentin tubule where the diffused cations and anions then react to form an insoluble precipitate which is bound to the tooth. As a result, when an effective amount of the divalent metal cations is used, the subsurface lesion is more effectively remineralized or desensitized and/or the exposed dentin tubule is more effectively mineralized.

The divalent metal salt(s) which can be used in the products of the present invention may be any water-soluble, non-toxic divalent metal compound which will stabilize the calcium, phosphate and fluoride ions so that these ions do not rapidly or prematurely precipitate before diffusing into the teeth. In practice, however, it has been found that at least one member selected from the group consisting of magnesium, strontium, tin, and zinc, with magnesium being preferred, is the most effective divalent metal in stabilizing the system.

Suitable magnesium compounds include, for example, magnesium acetate, magnesium ammonium sulfate, magnesium benzoate, magnesium bromide, magnesium borate, magnesium citrate, magnesium chloride, magnesium gluconate, magnesium glycerophosphate, magnesium hydroxide, magnesium iodide, magnesium oxide, magnesium propionate, magnesium D-lactate, magnesium DL-lactate, magnesium orthophosphate, magnesium phenolsulfonate, magnesium pyrophosphate, magnesium sulfate, magnesium nitrate, and magnesium tartrate. Preferred magnesium compounds are magnesium chloride, magnesium acetate and magnesium oxide.

Suitable strontium compounds include, for example, strontium acetate, strontium ammonium sulfate, strontium benzoate, strontium bromide, strontium borate, strontium caprylate, strontium carbonate, strontium citrate, strontium chloride, strontium gluconate, strontium glycerophosphate, strontium hydroxide, strontium iodide, strontium oxide, strontium propionate, strontium D-lactate, strontium DL-lactate, strontium pyrophosphate, strontium sulfate, strontium nitrate, and strontium tartrate. Preferred strontium compounds are strontium acetate, strontium chloride, strontium nitrate.

Suitable tin compounds include, for example, stannous acetate, stannous ammonium sulfate, stannous benzoate, stannous bromide, stannous borate, stannous carbonate, stannous citrate, stannous chloride, stannous gluconate, stannous glycerophosphate, stannous hydroxide, stannous iodide, stannous oxide, stannous propionate, stannous D-lactate, stannous DL-lactate, stannous orthophosphate, stannous pyrophosphate, stannous sulfate, stannous nitrate, and stannous tartrate. A preferred tin compound is stannous chloride.

Suitable zinc compounds include, for example, zinc acetate, zinc ammonium sulfate, zinc benzoate, zinc bromide, zinc borate, zinc citrate, zinc chloride, zinc gluconate, zinc glycerophosphate, zinc hydroxide, zinc iodide, zinc oxide, zinc propionate, zinc D-lactate, zinc DL-lactate, zinc pyrophosphate, zinc sulfate, zinc nitrate, and zinc tartrate. Preferred zinc compounds are zinc acetate, zinc chloride, zinc sulfate, and zinc nitrate.

In addition to the water-soluble orthophosphate salt(s), the anionic agglomerate component used in the present invention may further contain at least one water-soluble fluoride salt. Suitable water-soluble fluoride salts for use in the present invention include the alkali metal or ammonium fluorides such as sodium, potassium, lithium or ammonium fluoride; tin fluoride; indium fluoride; zirconium fluoride; copper fluoride; nickel fluoride; palladium fluoride; fluorozirconates such as sodium, potassium or ammonium fluorozirconate or tin fluorozirconate; fluorosilicates; fluoroborates; and fluorostannites. Although not preferred, fluorophosphates, such as sodium fluorophosphate, potassium fluorophosphate and ammonium fluorophosphate, are also suitable for use in the present invention. In addition, organic fluorides, such as the known amine fluorides, can also be used in the oral products of this invention.

Sodium fluoride is the preferred fluoride salt for use in the present invention.

In preferred embodiments of the present invention, the respective remineralizing/mineralizing amounts of the cationic and anionic agglomerate components are such as to provide a mixed aqueous solution composed of these salts with from about 100 ppm to about 15,000 ppm of dissolved calcium ions and from about 100 ppm to about 15,000 ppm of dissolved orthophosphate ions.

If a non-calcium divalent metal salt is used in the cationic agglomerate component, the amount of such salt used should be such as to provide the mixed aqueous solution with at least about 10 ppm, more preferably at least about 100 ppm, and most preferably from about 100 ppm to about 20,000 ppm of divalent metal cations.

To avoid fluorosis and other toxic effects, it is undesirable to ingest an average of more than about 0.2 mg of fluoride from all sources all day. Therefore, the concentration of fluoride provided in products of the invention should be appropriately limited. The concentration of fluoride ions in a chewing gum, tablet, or lozenge should be no more than about 100 ppm, preferably no more than 20 ppm, most preferably in the range of from 0.5 to 10 ppm. In edible foods, the purposeful addition of fluoride should be avoided.

The products of this invention preferably contain from about 0.05% to about 15.0% by weight, more preferably from about 0.10% to about 10.0% by weight, of the calcium salt(s), and from about 0.05% to about 15.0% by weight, more preferably from about 0.10% to about 10.0% by weight, of the orthophosphate salt(s). The product may further contain at least 0.0001%, preferably from about 0.001% to about 2.0%, and more preferably from about 0.01% to about 1.0%, by weight of the divalent metal salt(s).

The products of this invention contain a molar ratio of the calcium salt(s) to the orthophosphate salt(s) of preferably from about 0.01:1 to about 100:1. Most preferably, the concentration of the calcium salt(s) and the concentration of the orthophosphate salt(s) are preferably essentially the same in the products of this invention. The concentration of the calcium salt(s) may exceed the solubility of such salt, whereas the concentration of the orthophosphate salt(s) is usually as high or even higher than the solubility thereof.

The cationic and anionic agglomerate components used in the present invention have a pH in water such that a mixed aqueous solution formed by mixing these components with water and/or saliva has a pH of from about 4.5 to about 10.0, preferably from about 5.0 to about 7.0, more preferably from about 5.0 to about 5.75. At a pH within such range, enough of the calcium ions, orthophosphate ions and, if present, non-calcium divalent metal ions and fluoride ions in the mixed aqueous solution remain soluble for the period of time required to allow sufficient amounts of the ions to diffuse through the tooth surface so as to substantially remineralize the subsurface lesions and/or substantially mineralize the exposed tubules of the dental enamel. If the mixed aqueous solution has a pH below about 3, demineralization will occur rapidly because the concentration of calcium and phosphate in saliva is likely to be significantly below saturation. A pH below about 2.5 is undesirable from a safety standpoint.

The pH of the mixed aqueous solution may be adjusted to the desired pH by methods well known in the art. The pH may be lowered by the addition of any acid which is safe for use in the oral cavity and which yields the desired pH at the amount employed. Examples of suitable acids include acetic acid, phosphoric acid, citric acid, malic acid, gluconic acid and succinic acid. Alternatively, acidic phosphate salts can be used to produce an acidic pH and alkaline phosphate salts can be used to produce an alkaline pH.

As stated previously herein, the solid oral products of this invention are prepared by incorporating the cationic and anionic agglomerate components into a basic solid oral product, e.g., chewing gum, lozenge, and the like. An alternative way of preparing the product of this invention is to provide for two separate solid oral products (e.g., chewing gums or lozenges) which are then broken up into pieces. The pieces are then homogeneously mixed and compressed together to produce a single solid oral product (e.g., a single gum or lozenge) composed of separate zones containing the calcium and phosphate salts. For example, a lozenge can be prepared from two lozenges wherein one lozenge contains the calcium-containing composition and the second lozenge contains the phosphate-containing composition. The lozenges are then grinded into particles which are then homogeneously mixed and compressed into a single lozenge containing separate zones of calcium and orthophosphate salts.

The present invention further provides a method of remineralizing subsurface dental lesions and/or mineralizing exposed dentinal tubules using the oral product of this invention. The method of this invention involves the steps of:

(1) providing the oral product of this invention;
(2) causing the oral product to be mixed with water and/or saliva in the oral cavity so as to form a mixed aqueous solution having a pH of from about 4.5 to about 10.0 and containing calcium ions released by the calcium salt and orthophosphate ions released by the orthophosphate salt; and (3) promptly after formation of the mixed aqueous solution, applying the solution to the tooth for a period of time sufficient to allow a remineralizing amount of the calcium ions and a remineralizing amount of the orthophosphate ions to diffuse through the tooth to a subsurface area thereof, the diffused calcium ions and the diffused orthophosphate ions reacting at the subsurface area to form an insoluble calcium phosphate precipitate which is bound to the tooth, thereby remineralizing the subsurface lesion and/or mineralizing the exposed dentinal tubule.

The length of time in which the tooth is treated with the mixed aqueous solution is important to the present invention. The period of treatment needs to be long enough to allow diffusion of the ions through the tooth surface to the demineralized subsurface lesion(s) and/or exposed dentin tubule(s). Such period of treatment is preferably at least about 2 minutes, more preferably at least about 5 minutes, and most preferably at least about 15 minutes.

As stated previously herein, the ions which have diffused through the tooth surface form an insoluble precipitate on the demineralized subsurface lesion(s) and/or on the exposed dentin tubule(s). Although many precipitates are within the broad scope of this invention, it is preferred that the precipitate render the remineralized subsurface and/or mineralized dentin of the tooth treated in accordance with this invention more resistant to demineralization than was the original enamel. Thus, the preferred precipitate is one which is less soluble than the original enamel. Tooth enamel primarily contains a slightly carbonated apatite. If the precipitating species is not carbonated, the precipitate will be somewhat less soluble than the original enamel. Therefore, when fluoride anions are not present, it is desirable that conditions be present which favor the precipitation of unsubstituted hydroxyapatite. Thus, for example, it is desirable to avoid the addition of carbonates or bicarbonates to non-fluoride compositions. On the other hand, if fluoride salts are used in the products of this invention, the apatite will incorporate fluoride anions, thus rendering the precipitate more resistant to demineralization than was the original enamel. However, even when fluoride anions are not directly added to the remineralizing/mineralizing mixed aqueous composition used in the present invention, it has been found that the teeth treated with such composition will absorb more fluoride when subsequently treated with a fluoride-containing product (e.g., a fluoride toothpaste) than teeth which had not been pretreated with such composition.

Thus, the precipitate formed in the present invention is preferably a calcium phosphate or a hydroxyapatite.

Therefore, use of the products of this invention not only remineralizes the demineralized enamel and/or mineralize the exposed dentin tubules but also renders such remineralized enamel and/or mineralized dentin tubule more resistant to subsequent demineralization than was the original enamel or tubule.

The mixed aqueous solution formed from the products of this invention and the insoluble precipitate formed from the mixed aqueous solution must both have acceptable levels of toxicity. In other words, the particular ions, in the amounts used in the remineralization and/or mineralization process, must be non-toxic. Furthermore, such solution and precipitate should be otherwise compatible in the oral environment.

As mentioned previously herein, the solid product of this invention may be in the form of a chewing gum, a lozenge, a candy, an edible food product, a tablet, a toothpowder, and the like. In preferred embodiments, the solid product of this invention is a chewing gum or lozenge, more preferably a chewing gum.

Chewing gums are the preferred vehicles for delivering the cationic and anionic components of the present invention because the inherent nature of chewing gums allows prolonged contact with the teeth and, further, because the gum base can provide sustained release of the anionic and cationic components of the products of this invention, thus minimizing the amount of the anionic and cationic components that must be used.

Chewing gum products within the scope of this invention may be any of a variety of different chewing gums, bubble gums, dragees, and the like, including low or high moisture, sugar or sugarless, wax-containing or wax-free, low calorie (via high base or low calorie bulking agents), and/or may contain other dental health agents.

Chewing gum generally consists of a water-insoluble gum base, a water-soluble portion and flavors. The water-soluble portion dissipates with a portion of the flavor over a period of time during chewing. The gum base portion is retained in the mouth throughout the chew.

The insoluble gum base generally contains elastomers, resins, fats and oils, softeners, and inorganic fillers. The gum base may or may not include wax. The insoluble gum base can constitute from about 5% to about 95%, preferably from about 10% to about 50%, more preferably from about 20% to about 35%, by weight of the chewing gum.

In one embodiment, the chewing gum base which can be used in the present invention contains from about 20% to about 60% by weight of a synthetic elastomer, from 0% to about 30% by weight of a natural elastomer, from about 5% to about 55% by weight of an elastomer plasticizer, from about 4% to about 35% by weight of a filler, from about 5% to about 35% by weight of a softener, and, optionally, minor amounts (about 1% by weight or less) of miscellaneous ingredients such as colorants, antioxidants, and the like.

Synthetic elastomers suitable for use herein include but are not limited to polyisobutylene with GPC weight average molecular weight of from about 10,000 to about 95,000, preferably from about 50,000 to about 80,000; isobutylene-isoprene copolymer (butyl elastomer); styrene-butadiene copolymers having styrene-butadiene ratios of from about 1:3 to about 3:1, preferably from about 1:1 to about 1:3; polyvinyl acetate having a GPC weight average molecular weight of from about 2000 to about 90,000, preferably from about 10,000 to about 65,000; polyisoprene; polyethylene; vinyl acetate-vinyl laurate copolymer having a vinyl lauryl content of from about 5% to about 50% by weight, preferably from about 10% to about 45% by weight, of the copolymer, and combinations thereof.

Non-limiting examples of suitable natural elastomers include natural rubber such as smoked or liquid latex and guayule as well as natural gums such as jelutong, lechi caspi, perillo, sorva, massaranduba balata, massaranduba chocolate, nispero, rosindinha, chicle, gutta hang kang, and combinations thereof. Preferred natural elastomers include jelutong, chicle, sorva, and massaranduba balata.

The preferred concentrations of the synthetic elastomer and the natural elastomer will vary depending on whether the chewing gum in which the base is used is adhesive or conventional, bubble gum or regular gum, as discussed below.

Non-limiting examples of suitable elastomer plasticizers include natural rosin esters such as glycerol esters of partially hydrogenated rosin, glycerol esters polymerized rosin, glycerol esters of partially dimerized rosin, glycerol esters of rosin, penta-erythritol esters of partially hydrogenated rosin, methyl and partially hydrogenated methyl esters of rosin, pentaerythritol esters of rosin; synthetics such as terpene resins derived from alpha-pinene, beta-pinene, and/or d-limonene; and any suitable combinations of the foregoing. The preferred elastomers will also vary depending on the specific application, and on the type of elastomer which is used.

Non-limiting examples of suitable fillers/texturizers include magnesium and calcium carbonate; ground limestone; silicate types such as magnesium and aluminum silicate; clay; alumina; talc; titanium oxide; mono-, di- and tri-calcium phosphate; cellulose polymers, such as wood; and combinations thereof.

Non-limiting examples of suitable softeners/emulsifiers include tallow; hydrogenated tallow; hydrogenated and partially hydrogenated vegetable oils; cocoa butter; glycerol monostearate; glycerol triacetate; lecithin; mono-, di-, and triglycerides; acetylated monoglycerides; fatty acids such as stearic acid, palmitic acid, oleic acid and linoleic acid; and combinations thereof.

Suitable colorants and whiteners include, e.g., FD&C-type dyes and lakes, fruit and vegetable extracts, titanium dioxide and combinations thereof.

The base may or may not include wax.

In addition to a water-insoluble gum base portion, a typical chewing gum product includes a water-soluble bulk portion and one or more flavoring agents. The water-soluble portion can include, e.g., bulk sweeteners, high intensity sweeteners, flavoring agents, softeners, emulsifiers, colors, acidulants, fillers, antioxidants, and other components that provide desired attributes.

Softeners are added to chewing gum products to optimize the chewability and mouth feel of the gum. The softeners, which are also known as plasticizers and plasticizing agents, generally constitute from about 0.5% to about 15% by weight of the chewing gum. The softeners may include, e.g., glycerin, lecithin, and combinations thereof. Aqueous sweetener solutions such as those containing sorbitol, hydrogenated starch hydrolysates, corn syrup and combinations thereof, may also be used as softeners and binding agents in chewing gum products.

Bulk sweeteners include both sugar and sugarless components. The bulk sweetener(s) preferably constitutes from about 5% to about 95% by weight, more preferably from about 20% to about 80% by weight, and most preferably from about 30% to about 60% by weight, of the chewing gum.

Sugar sweeteners generally include saccharide-containing components such as, e.g., sucrose, dextrose, maltose, dextrin, dried invert sugar, fructose, levulose, galactose, corn syrup solids, and the like, alone or in combination.

Sugarless sweeteners include, e.g., sugar alcohols such as sorbitol, mannitol, xylitol, hydrogenated starch hydrolysates, maltol, and the like, alone or in combination.

High intensity artificial sweeteners can also be used, alone or in combination with the above. Non-limiting examples of such sweeteners include sucralose, aspartame, salts of acesulfame, alitame, saccharin and its salts, cyclamic acid and its salts, glycyrrhizin, dihydrochalccones, thaumatin, monellin, and the like, alone or in combination. To provide longer lasting sweetness and flavor perception, it may be desirable to encapsulate or otherwise control the release of at least a portion of the artificial sweetener. Such techniques as wet granulation, wax granulation, spray drying, spray chilling, fluid bed coating, coacervation, and fiber extension may be used to achieve the desired release characteristics.

The amount of the artificial sweetener used will vary greatly and will depend on such factors as potency of the sweetener, rate of release, desired sweetness of the product, level and type of flavor used, and cost considerations. Thus, the active level of the artificial sweetener may vary from about 0.02% to about 8.0% by weight. When carriers used for encapsulation are included, the amount of the encapsulated sweetener used will be proportionately higher.

The chewing gum of this invention may be either sugarless or sugar-containing. Alternatively, the chewing gum may contain combinations of sugar and/or sugarless sweeteners. While ordinary sugars, e.g., sucrose, can be used in the invention, it is preferable to avoid them because of their cariogenic nature. Non-fermentable sugars such as sorbitol are preferred. Additionally, a softener may be added which provides additional sweetness such as with aqueous sugar or alditol solutions.

If a low calorie gum is desired, a low caloric bulking agent can be used. Non-limiting examples of such low calorie bulking agents include polydextrose, raftilose, raftilin, fructooligosaccharides, palatinose oligosaccharides, guar gum hydrolysates, or indigestible dextrin.

Suitable flavoring agents include those which have been previously described herein.

The flavoring agent can be used in the chewing gum of this invention in an amount preferably ranging from about 0.1% to about 15.0% by weight, more preferably from about 0.2% to about 5.0% by weight.

The chewing gum may also contain a dental abrasive. Dental abrasives are particularly valuable in chewing gums because of the polishing action which occurs during chewing. The term "dental abrasives" as used herein includes all manner and form of such materials which are normally used in toothpastes, chewing gums and the like. The preferred dental abrasive for use in this invention is dicalcium diphosphate dihydrate, which also serves as an alkaline buffer. Other non-limiting examples of suitable dental abrasives include calcium carbonate, sodium metaphosphate, aluminum hydroxide, magnesium carbonate, calcium sulphate, silicas such as aerogels and xerogels, and tricalcium phosphate. The dental abrasive is preferably used in an amount of from about 1.0% to about 30.0% by weight, more preferably from about 1.5% to about 20.0% by weight.

The chewing gum of this invention may also contain glycerine, which serves to soften and maintain the chewability of the chewing gum for prolonged periods and also adds to the sweetness of the chewing gum. The glycerine is preferably used in an amount of from about 0.01% to about 10.0% by weight, more preferably from about 0.2% to about 5.0% by weight of the chewing gum.

EXPERIMENTAL

Examples 1–4 illustrate agglomerated compositions which can be used in the remineralizing chewing gums of the present invention.

EXAMPLE 1

In Example 1, cationic and anionic agglomerate particles are prepared from the ingredients set forth in Table I below.

TABLE I

Example 1: Agglomerate Particle Ingredients

| Ingredient | Cationic Part (wt. %) | Anionic Part (wt. %) |
| --- | --- | --- |
| Sorbitol | 60.00 | 60.00 |
| Calcium Acetate | 40.00 | 0 |
| Monosodium Orthophosphate | 0 | 40.00 |

The ingredients in the cationic part are initially mixed and compressed by any means, e.g., passage through a chilsonator (Fitzpatrick) to form a solid sheet or passage through a tablet press. The resulting solid materials are then ground to a desirable particle size of from about 50 to about 500 microns.

Similarly, the ingredients in the anionic part are mixed and compressed in the same manner as was done with the ingredients in the cationic part, the resulting solid materials also being ground to a desirable particle size of from about 50 to about 500 microns.

The agglomerated cationic and anionic particles are then added to a conventional chewing gum base to form a chewing gum product containing about 2.5% by weight of the cationic particles, about 2.5% by weight of the anionic particles, and about 95.0% by weight of the conventional chewing gum ingredients.

EXAMPLE 2

In Example 2, cationic and anionic agglomerate particles are prepared from the ingredients set forth in Table II below.

TABLE II

Example 2: Agglomerate Particle Ingredients

| Ingredient | Cationic Part (wt. %) | Anionic Part (wt. %) |
| --- | --- | --- |
| Sorbitol | 40.00 | 50.00 |
| Xylitol | 20.00 | 0 |
| Malic Acid | 0 | 5.00 |
| Calcium Lactate | 40.00 | 0 |
| Monoammonium Phosphate | 0 | 45.00 |

The mixing and compressing steps followed in Example 1 above are repeated in Example 2. The solid materials formed from the mixing and compressing of the cationic part ingredients are ground to a particle size of from about 50 to about 500 microns. Likewise, the solid materials formed from the mixing and compressing of the anionic part ingredients are also ground to a particle size of from about 50 to about 500 microns.

The agglomerated cationic and anionic particles are then added to a conventional chewing gum base to form a chewing gum product containing about 8.0% by weight of the cationic particles, about 2.0% by weight of the anionic particles, and about 90.0% by weight of the conventional chewing gum ingredients.

EXAMPLE 3

In Example 3, cationic and anionic agglomerate particles are prepared from the ingredients set forth in Table III below.

TABLE III

Example 3: Agglomerate Particle Ingredients

| Ingredient | Cationic Part (wt. %) | Anionic Part (wt. %) |
| --- | --- | --- |
| Sorbitol | 40.00 | 60.00 |
| Mannitol | 20.00 | 0 |
| Sodium Bicarbonate | 0 | 5.00 |
| Calcium Sulfate | 40.00 | 0 |
| Dipotassium Phosphate | 0 | 35.00 |

The mixing and compressing steps followed in Examples 1 and 2 above are repeated in Example 3, with the solid materials formed from the cationic and anionic part ingredients being ground to a desirable particle size of between about 50 and about 500 microns.

The agglomerated cationic and anionic particles are then added to a conventional chewing gum base to form a chewing gum product containing about 6.0% by weight of the cationic particles, about 4.0% by weight of the anionic particles, and about 90.0% by weight of the conventional chewing gum ingredients.

EXAMPLE 4

In Example 4, cationic and anionic agglomerate particles are prepared from the ingredients set forth in Table IV below.

TABLE IV

Example 4: Agglomerate Particle Ingredients

| Ingredient | Cationic Part (wt. %) | Anionic Part (wt. %) |
| --- | --- | --- |
| Carbowax 8000 | 25.00 | 30.00 |
| Xylitol | 10.00 | 0 |
| Calcium Chloride | 65.00 | 0 |
| Monopotassium Phosphate | 0 | 70.00 |

The mixing and compressing steps followed in Examples 1, 2 and 3 are repeated in Example 4. The solid particles are ground to a particle size of between about 50 and about 500 microns.

The agglomerated cationic and anionic particles are then added to a conventional chewing gum base to form a chewing gum product containing about 5.0% by weight of the cationic particles, about 2.0% by weight of the anionic particles, and about 93.0% by weight of the conventional chewing gum ingredients.

What is claimed is:

1. A chewing gum product capable of effecting remineralization of subsurface dental lesions and/or mineralization of exposed dentinal tubules, comprising:
   (A) a discrete cationic agglomerate component comprising at least one water-soluble or partially water soluble calcium salt and a first inert solid carrier;
   (B) a discrete cationic agglomerate component comprising at least one water soluble orthophosphate salt and a second inert solid carrier; and
   (C) a gum base containing said components (A) and (B); wherein components (A) and (B) have a pH in water such that a mixed aqueous solution formed by mixing components (A) and (B) with water and/or saliva has a pH of from about 4.50 to about 10.0;

further wherein the cationic and anionic agglomerate components keep said calcium salt and said orthophosphate salt from reacting prior to use and are simultaneously releasable from the gum base upon mixing of the product with water and/or saliva to form the mixed aqueous solution such that the mixed aqueous solution comprises calcium cations released from the calcium salt and orthophosphate anions released by the orthophosphate salt.

2. A product according to claim 1, wherein one or both of the first and second solid inert carriers is selected from the group consisting of sorbitol, mannitol, and xylitol.

3. A product according to claim 1, wherein one or both of the first and second solid inert carriers is an insoluble silica or an insoluble calcium phosphate.

4. A product according to claim 3, wherein the insoluble calcium phosphate is selected from the group consisting of dicalcium phosphate dihydrate, anhydrous dicalcium phosphate, tricalcium phosphate and calcium hydroxyapatite.

5. A product according to claim 1, wherein one or both of the cationic and anionic agglomerate components further comprises a binder.

6. A product according to claim 5, wherein said binder is a polymer selected from the group consisting of polyvinyl acetate, PVP and carboxymethyl cellulose.

7. A product according to claim 1, wherein the cationic and anionic agglomerate components each have an average particle size ranging from about 20 to about 500 microns.

8. A product according to claim 1, wherein the cationic and anionic agglomerate components each have an average particle size ranging from about 30 to about 100 microns.

9. A product according to claim 1, wherein the product has a smooth consistency and the cationic and anionic agglomerate components each have an average particle size of from about 30 to about 50 microns.

10. A product according to claim 1, wherein the product has a crunchy consistency and the cationic and anionic agglomerate components each have an average particle size of from about 50 to about 80 microns.

11. A product according to claim 1, wherein components (A) and (B) have a pH in water such that the mixed aqueous solution has a pH of from about 5.0 to about 8.0.

12. A product according to claim 1, wherein components (A) and (B) have a pH in water such that the mixed aqueous solution as a pH of from about 5.5 to about 7.0.

13. A product according to claim 1, wherein the calcium salt is a water-soluble calcium salt selected from the group consisting of calcium chloride, calcium nitrate, calcium acetate, calcium lactate, calcium gluconate, and mixtures thereof.

14. A product according to claim 1, wherein the calcium salt is calcium nitrate.

15. A product according to claim 1, wherein the calcium salt is a partially water-soluble calcium salt selected from the group consisting of calcium sulfate, anhydrous calcium sulfate, calcium sulfate hemihydrate, calcium sulfate dihydrate, calcium malate, calcium tartarte, calcium malonate and calcium succinate.

16. A product according to claim 1, wherein the calcium salt is calcium sulfate.

17. A product according to claim 1, wherein the orthophosphate salt is selected from the group consisting of alkali metal salts of orthophosphoric acid and ammonium salts of orthophosphoric acid.

18. A product according to claim 1, wherein the orthophosphate salt is selected from the group consisting of potassium orthophosphate, sodium orthophosphate, ammonium orthophosphate, monopotassium orthophosphate, dipotassium orthophosphate, tripotassium orthophosphate, monosodium orthophosphate, disodium orthophosphate and trisodium orthophosphate.

19. A product according to claim 1, wherein the cationic agglomerate component further comprises at least one non-toxic divalent metal salt other than a calcium salt.

20. A product according to claim 1, wherein the anionic agglomerate component further comprises at least one water-soluble fluoride salt.

* * * * *

UNITED STATES PATENT AND TRADEMARK OFFICE
CERTIFICATE OF CORRECTION

PATENT NO.    : 6,440,394 B2
DATED         : August 27, 2002
INVENTOR(S)   : Barth et al.

It is certified that error appears in the above-identified patent and that said Letters Patent is hereby corrected as shown below:

Column 16,
Line 63, change "cationic" to -- anionic --.

Signed and Sealed this

Third Day of December, 2002

JAMES E. ROGAN
*Director of the United States Patent and Trademark Office*